United States Patent
Hölzer et al.

[11] Patent Number: 5,824,782
[45] Date of Patent: Oct. 20, 1998

[54] IMMUNOCONJUGATES II

[75] Inventors: Wolfgang Hölzer, Darmstadt; Ilka von Hoegen, Doffenheim; Wolfgang Strittmatter, Ober-Ramstadt; Siegfried Matzku, Zwingenberg, all of Germany

[73] Assignee: Merck Patent Gesellschaft mit beschrankter Haftung, Germany

[21] Appl. No.: 528,523

[22] Filed: Sep. 15, 1995

[30] Foreign Application Priority Data

Sep. 16, 1994 [EP] European Pat. Off. .............. 94114572

[51] Int. Cl.⁶ .......................... A61K 38/00; C07K 16/00; C07K 17/00; C07K 17/14

[52] U.S. Cl. ...................... 530/391.1; 530/391.5; 530/391.7; 530/391.9; 514/12; 424/181.1; 424/179.1; 424/178.1; 435/69.7; 435/71.1; 536/23.4

[58] Field of Search .................. 435/69.7, 71.1; 424/178.1, 179.1, 181.1; 536/23.4; 530/391.1, 391.5, 391.7, 391.9; 514/12

[56] References Cited

U.S. PATENT DOCUMENTS

| | | | |
|---|---|---|---|
| 5,112,946 | 5/1992 | Maione | 530/324 |
| 5,314,995 | 5/1994 | Fell et al. | 530/351 |
| 5,470,571 | 11/1995 | Herlyn et al. | 424/1.49 |

FOREIGN PATENT DOCUMENTS

| | | |
|---|---|---|
| 0 396 387 A2 | 11/1990 | European Pat. Off. . |
| 0 439 095 | 7/1991 | European Pat. Off. . |
| 0 586 002 | 3/1994 | European Pat. Off. . |
| 91/14438 | 10/1991 | WIPO . |
| WO 92/08495 | 5/1992 | WIPO . |
| WO 92/15683 | 9/1992 | WIPO . |
| WO 93/00917 | 1/1993 | WIPO . |

OTHER PUBLICATIONS

Baggiolini et al. J. Clin. Invest. 84:1045–1049, Oct. 1989.
Reisser et al. Anticancer Res. 14:977–980, Jun. 1994.
"Growth Factor Receptors as Targets for Antitumor Therapy with Monoclonal Antibodies," Waldmann et al., *Monoclonal Antibody Therapy. Prog. Allergy*, vol. 45, 1988, pp. 147–160.
Naramura et al., Chem. Abstract, vol. 120, No. 21, May 23, 1994.

*Primary Examiner*—Sheela Huff
*Attorney, Agent, or Firm*—Millen, White, Zelano & Branigan, P.C.

[57] ABSTRACT

The invention provides new immunoconjugates comprising a mono-clonal antibody or a fragment thereof specific for the human EGF-receptor molecule and a member of the chemokine family, preferably selected from the C-X-C family, e.g. lnterleukin-8 (IL-8). The immunoconjugates induce cytotoxic and chemotactic activity and are suitable for a targeted tumor therapy.

13 Claims, 6 Drawing Sheets

SEQUENCE LISTING ( 1 ) GENERAL INFORMATION:

( i i i ) NUMBER OF SEQUENCES: 13

( 2 ) INFORMATION FOR SEQ ID NO: 1:

( i ) SEQUENCE CHARACTERISTICS:
        ( A ) LENGTH: 15 base pairs
        ( B ) TYPE: nucleic acid ( C ) STRANDEDNESS: single
            ( D ) TOPOLOGY: linear ( i i ) MOLECULE TYPE: other nucleic acid
            ( A ) DESCRIPTION: /desc = "c- gamma1CH2/IL-8 junction"

( i i i ) HYPOTHETICAL: NO ( x i ) SEQUENCE DESCRIPTION: SEQ ID NO: 1:

AAAGCCATGG GTGCT                                                                                          15

( 2 ) INFORMATION FOR SEQ ID NO: 2:

( i ) SEQUENCE CHARACTERISTICS:
            ( A ) LENGTH: 5 amino acids
            ( B ) TYPE: amino acid
            ( C ) STRANDEDNESS: single
            ( D ) TOPOLOGY: linear ( i i ) MOLECULE TYPE: protein ( i i i ) HYPOTHETICAL: NO ( v ) FRAGMENT TYPE: internal ( x i ) SEQUENCE DESCRIPTION: SEQ ID NO: 2:

Lys  Ala  Met  Gly  Ala
      1                   5

( 2 ) INFORMATION FOR SEQ ID NO: 3:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "c- gamma1CH2/IL-8 junction"

( i i i ) HYPOTHETICAL: NO ( x i ) SEQUENCE DESCRIPTION: SEQ ID NO: 3:

GCCAAAGTGA TCAAAGAA                                                                                       18

( 2 ) INFORMATION FOR SEQ ID NO: 4:

( i ) SEQUENCE CHARACTERISTICS:
            ( A ) LENGTH: 6 amino acids
            ( B ) TYPE: amino acid
            ( C ) STRANDEDNESS: single
            ( D ) TOPOLOGY: linear ( i i ) MOLECULE TYPE: protein ( i i i ) HYPOTHETICAL: NO ( v ) FRAGMENT TYPE: internal ( x i ) SEQUENCE DESCRIPTION: SEQ ID NO: 4:

Gly  Lys  Val  Ile  Lys  Glu
      1                   5

( 2 ) INFORMATION FOR SEQ ID NO: 5:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: other nucleic acid -continued (A) DESCRIPTION: /desc = "c- gamma1 5'primer"

(i i i) HYPOTHETICAL: NO (x i) SEQUENCE DESCRIPTION: SEQ ID NO: 5:

CAGGAAACAG CTATGAC 17

(2) INFORMATION FOR SEQ ID NO: 6:

(i) SEQUENCE CHARACTERISTICS:
(A) LENGTH: 30 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "c- gamma1 3'primer"

(i i i) HYPOTHETICAL: NO (x i) SEQUENCE DESCRIPTION: SEQ ID NO: 6:

TGATCCATGG CTTTGGAGAT GGTTTTCTCG 30

(2) INFORMATION FOR SEQ ID NO: 7:

(i) SEQUENCE CHARACTERISTICS:
(A) LENGTH: 27 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "IL-8 5'primer"

(i i i) HYPOTHETICAL: NO (x i) SEQUENCE DESCRIPTION: SEQ ID NO: 7:

GATCTACCTG CCATGGGTGC TAAAGAA 27

(2) INFORMATION FOR SEQ ID NO: 8:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "IL-8 3'primer"

(i i i) HYPOTHETICAL: NO (x i) SEQUENCE DESCRIPTION: SEQ ID NO: 8:

GTAAAACGAC GGCCAGT 17

(2) INFORMATION FOR SEQ ID NO: 9:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "c- gamma1 5'primer"

(i i i) HYPOTHETICAL: NO (x i) SEQUENCE DESCRIPTION: SEQ ID NO: 9:

CAGGAAACAG CTATGAC 17

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "c- gamma1 3'primer"

(iii) HYPOTHETICAL: NO

(xi) SEQUENCE DESCRIPTION: SEQ ID NO:10:

CGCGTGATCA CTTTGGCTTT GGAGATGGTT    30

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Il-8 5'primer"

(iii) HYPOTHETICAL: NO

(xi) SEQUENCE DESCRIPTION: SEQ ID NO:11:

CTCGTGATCA AAGAACTTAG ATGTCAATGC    30

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Il-8 3'primer"

(iii) HYPOTHETICAL: NO

(xi) SEQUENCE DESCRIPTION: SEQ ID NO:12:

GTAAAACGAC GGCCAGT    17

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS: single
        (D) TOPOLOGY: linear     (ii) MOLECULE TYPE: protein     (iii) HYPOTHETICAL: NO     (v) FRAGMENT TYPE: internal     (xi) SEQUENCE DESCRIPTION: SEQ ID NO:13:

Gly Gly Gly Gly Ser
    1               5

IMMUNOCONJUGATES II

BACKGROUND OF THE INVENTION

The present invention relates to new fusion proteins which consist of a tumor-associated targeting element, preferably a monoclonal antibody or a fragment thereof, recognizing and specific for a molecule which is preferentially expressed on human tumor cells such as the human epidermal growth factor receptor (EGFR), and a biologically active ligand selected from the group of chemokine proteins, preferably from the C-X-C family. The resulting fusion proteins may be used to deliver the biologically active ligand to a specific target cell or tissue. The new immunoconjugates can be used in tumor therapy and diagnostics.

A variety of therapeutic concepts have been used for the treatment of cancer patients. In the past, clinical trials have been performed with monoclonal antibodies which recognize specifically or preferentially cell-surface molecules expressed on malignant cells. The aim of this approach is the induction of antibody-dependent cellular cytoxicity (ADCC) or complement-mediated cytotoxicity to eliminate tumor cells. A second approach is the cytokine-mediated activation of an immune response. The cytokine-induced anti-tumor activity can be mediated by:

1) a direct cytotoxic/cytostatic effect of the cytokine on tumor growth;
2) tumor-antigen non-specific mechanisms such as LAK activity or monocyte/granulocyte mediated cytotoxicity; and/or
3) tumor-antigen specific immune responses mediated by CD4 and CD8-positive T-cells.

In this situation, a systemic immunity against the tumor has been observed in animal models.

However, cytotoxicity of high doses of the cytokines and insufficient in situ presence lead to the concept of targeted tumor therapy. The principle of targeted tumor therapy is based on the physical linkage of a target molecule such as a monoclonal antibody specific for a tumor-associated antigen with a biologically active effector molecule. The delivery of effector molecules by a target molecule should increase the cytokine concentration in the tumor and reduce the maximum dose required. In animal models it was demonstrated that in situ presence of the cytokine either by intratumoral injection or by secretion of transfected tumor cells may lead to tumor regression (for reviews see: Colombo and Forni, Immunology Today 15:48–51, 1994). In these systems, cytokines do not impair tumor proliferation, but are capable of activating a rapid and potent anti-tumor reaction. Therefore, the physical combination of an effector molecule and a targeting element represents a means of reducing the peripheral presence and enhancing the intratumoral availability of the biologically active ligand. Furthermore, single tumor cells or micro-metastases can also be targeted by these molecules.

The biologically active ligand for an antibody-directed targeting should induce the destruction of the target cell either directly or by creating an environment lethal to the target cell. This can be achieved by cytokines such as IL-1, IL-2, IL-4, IL-6, IL-7, IL-10, IL-13, IFNs, TNF and CSFs. These cytokines have been shown to elicit anti-tumor effect either directly or indirectly by activating host defense mechanisms (Mire-Sluis, TIBTECH 11:74–77, 1993; Colombo et al., Cancer Res. 52:4853–4857, 1992; Thomas & Balkwill, Pharmac. Ther. 52:307–330, 1991).

However, most of these cytokines activate effector cells, but show no or only weak chemotactic activity for them, so that anti-tumor activity may be weak in the absence of suitable amounts of effector cells at the tumor tissue.

Chemokines, however, are chemotactic for many effector cells and thus will enhance their presence at the tumor site, and secondly, they induce a variety of effector cell functions (see for example: Miller and Krangel (1992), "Biology and Biochemistry of the Chemokines: A Novel Family of Chemotactic and Inflammatory Cytokines", Critical Reviews in Immunology 12, 17).

IL-8, MIP $2\alpha$ (also known as GRO-$\beta$) and MIP $2\beta$ (GRO-y) are members of the $\alpha$- or C-X-C chemokine superfamily (also known as small cytokine superfamily or intercrines). They act as chemotactic factors and activate effector cell functions and might therefore represent optimal effector molecules. This family of C-X-C chemokines is a group of recently characterized small (8–10 kD) proteins, which show 20 to 50% homology in amino acid sequence and have chemotactic and pro-inflammatory activities. IL-8 has a well defined three dimensional structure (Clore et al., Biochemistry 29:1689—1696, 1990) and shares an N-terminal ELR motif with some of the C-X-C chemokines. It is to be expected that due to the sequence homology among the C-X-C chemokines, the three dimensional structure will be quite similar. This was already demonstrated for MCAF/MCP-1 (Gronenborn & Clore, Prot. Eng. 4:263–269, 1991).

The members of the C-X-C-group that have been described so far, act mainly on neutrophil granulocytes. The genes have been localized on chromosome 4. Members of this group include PF4, platelet basic protein, hIP10, IL-8, MIP $2\alpha$ and MIP $2\beta$. The effects of these proteins on neutrophils include chemotactic activity, degranulation and respiratory burst (Sherry and Cerami, Current opinion in Immunology 3:56–60, 1991; Oppenheim et al., Annu. Rev. Immunol. 9:617–648, 1991; Miller and Krangel, Critical Reviews in Immunology 12:17–46, 1992; Clark-Lewis et al., J. Biol. Chem. 266:23128–23134, 1991).

Members of the closely related $\beta$- or C-C-family of chemokines act mainly on monocytes. Their genes are all located on chromosome 17. These proteins include LD 78, Act-2, MCAF, 1309 and RANTES. These molecules show a strong chemotactic activity on monocytes (Matsushima et al., Chem. Immunol. 51:236–265, 1992; Oppenheim et al., Annu. Rev. Immunol. 9:617–648, 1991).

Recently, the anti-tumor potential of TCA3, a member of the $\beta$ chemokine family has been demonstrated in a mouse tumor model (Laning et al., J. Immunol. 153:4625–4635, 1994). Secretion of TCA3 by tumor cells resulted in an early infiltrate of neutrophils and monocytes accompanied by tumor necrosis. A tumor-specific and long-lasting immunity was observed in those animals that showed complete tumor regression. A host-mediated anti-tumor response was also induced by tumor cells secreting the a chemokine IP-10. The cellular infiltrates consisted of monocytes, neutrophils and lymphocytes (Luster and Leder, J. Exp. Med. 178:1057–1065, 1993). Neutrophils may play a role in both the priming and effector phases of the anti-tumor response: in vivo depletion of neutrophils abrogated rejection of syngeneic tumors in rats and the growth of subsequently transplanted identical tumors was not inhibited in contrast to non-depleted animals (Midorikawa et al., Cancer Res. 50:6243–6247, 1990).

Epidermal growth factor (EGF) is a polypeptide hormone which is mitogenic for epidermal and epithelial cells. When EGF interacts with sensitive cells, it binds to membrane receptors (EGFR). The EGFR is a transmembrane glycoprotein of about 170 kD, and is a gene product of the c-erb-B proto-oncogene.

The murine monoclonal antibody MAb 425 was raised against the human A431 carcinoma cell line (ATCC CRL 1555) and was found to bind to a polypeptide epitope on the external domain of the EGFR. It inhibits the binding of EGF and mediates tumor cytotoxicity in vitro and suppresses tumor cell growth of epidermal and colorectal carcinoma-derived cell lines in vitro (Rodeck et al., 1987, Cancer Res. 47:3692). Humanized and chimeric versions of MAb 425 are known from WO 92/15683.

Thus, it was an object of this invention to create an immunoconjugate having an EGFR antigen-binding antibody function, as well as having a biologically active ligand function, which has a high chemotactic activity for their effector cells, thus providing an effective low-toxicity targeted tumor therapy. Such immunoconjugates would provide an improvement over analogous cytokine-antibody immunoconjugates, which are similarly effective with respect to their ability to cause tumor lysis but not with respect to the possibility to effectively attract effector cells to a specific site by chemotactic properties.

SUMMARY OF THE INVENTION

The invention relates to fusion proteins which combine part of a monoclonal antibody, minimally the antigen-recognition site, or a complete monoclonal antibody recognizing and specific for an epitope of EGFR, with a biologically active ligand selected from the group of chemokines, preferably from the C-X-C family, especially IL-8. The constructs encoding these fusion proteins are generated by recombinant DNA technology methods. The fusion proteins contain the variable region of the antibody heavy chain and the CH1 domain of the constant region (CH1-conjugates, Fab-fragment) and the appropriate light chain, or the variable region of the antibody heavy chain and the CH1 and CH2 domain of the constant region, or the variable region of the antibody heavy chain and the CH1, CH2 and CH3 domain of the constant region, fused to the biologically active ligand in each case. By co-expression with the appropriate light chain, a fusion protein can be generated which targets antigen-bearing cells and delivers an active ligand to a specific site in the body.

Figure 1:
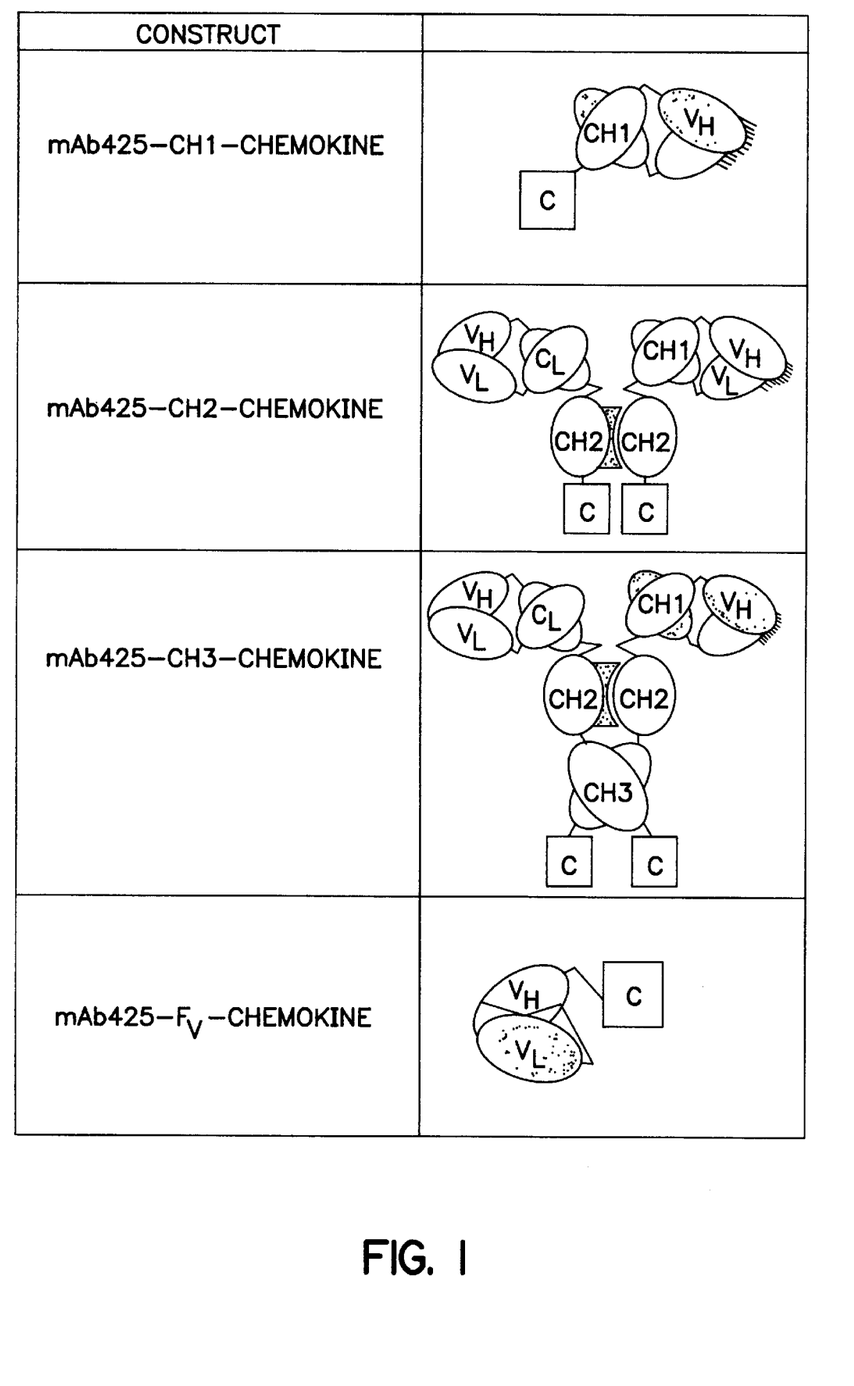

Analogously, another immunoconjugate can be obtained by fusing the chemokine to the C-terminus of a Fv-fragment of the antibody. In this case, heavy and light chains are expressed in one polypeptide, where both elements are combined by an appropriate linker sequence to ensure proper folding of the antigen binding site. The different constructs are shown in FIG. 1.

Expression of immunoconjugates results in new molecules which combine two functions: firstly, they target antigen-bearing cells (e.g., tumor cells which express EGFR on the surface of the cells) and secondly, they deliver a biologically active ligand to a specific site in the body. These ligands are potent chemoattractants and activating molecules and result in infiltration of effector cells at the tumor site which can effect subsequent tumor destruction. Thus, by means of the immunoconjugates according to the invention, tumors, such as melanoma, glioma, and carcinoma, can be detected and treated successfully in the absence of significant general toxic effects. Thus, it is an object of this invention to provide an immunoconjugate comprising of a monoclonal antibody or a fragment thereof directed to a tumor cell bearing an antigen epitope of the epidermal growth factor receptor (EGFR), and a chemokine protein ligand which is fused to said antibody or antibody fragment.

There are different groups of chemokines, such as C-X-C and C-C chemokines. In a preferred embodiment according to the invention the chemokine protein is selected from the C-X-C family. Within the C-X-C family, IL-8 is a preferred embodiment of the invention. Therefore, it is another object of this invention to provide an immunoconjugate, wherein the chemokine protein is selected from the C-X-C family and is preferably Interleukin 8 (IL-8).

In solution, IL-8 forms stable dimers (Clore et al., Biochemistry 29:1689–1696, 1990); therefore, in a further embodiment of the invention, the immunoconjugate having IL-8 as the chemokine ligand, e.g., an F(ab')-IL-8 fusion protein, is dimerized by interaction of two IL-8 monomers to form a bivalent immunoconjugate, thereby strengthening the interaction of the fusion protein with the antigen.

The antibodies which can be used according to the invention are either whole antibodies or fragments thereof. Suitable fragments are Fvs, Fabs or F(ab')2s (CH1 antibody fragments, as the latter term is used herein), CH3 and CH2 antibody fragments (FIG. 1). Preferred embodiments are Fvs, CH1-, CH2 and CH3 antibody fragments. In principle, all antibodies which are directed to EGF receptors on tumor cell surfaces are suitable. However, monoclonal antibody 425 is a preferred embodiment.

It is an object of the present invention, therefore, to provide an immunoconjugate, wherein the antibody is a Fab fragment or a F(ab')2 fragment consisting essentially of the variable region of the antibody heavy chain, the CH1 domain of the constant region, and the appropriate light chain (antibody-CH1 conjugate); another immunoconjugate, wherein the antibody is an antibody fragment consisting essentially of the variable region of the antibody heavy chain, the CH1 and CH2 domains of the constant region, and the appropriate light chain (antibody-CH2 conjugate); another immunoconjugate, wherein the antibody is a complete antibody consisting essentially of the variable region of the antibody heavy chain, the CH1, CH2 and CH3 domains of the constant region and the appropriate light chain (antibody-CH3 conjugate); and, finally, a further immunoconjugate, wherein the antibody consists essentially of the variable region of the antibody heavy chain, the appropriate light chain and a polypeptide sequence which links the light and heavy chain (antibody-Fv conjugate).

Appropriate light chains include those which are compatible with and thus assemble with the respective heavy chain portion of the antibody or antibody fragments of the fusion proteins of the invention to form an antigen-binding region, and which retain their biological activity. In general, they comprise the naturally-occurring light chains of the anti-EGFR antibody from which the immunoconjugate is derived.

The DNA encoding the immunoconjugates according to the invention may comprise optionally a restriction site between the antibody (or fragment thereof) and the chemokine protein which makes it possible to introduce, for example, a specific linker peptide in order to ensure an optimal binding of the conjugate to the target epitope. Suitable linker peptides and methods to introduce them are well known in the art and described below. According to the invention a restriction site is selected which is unique in the particular DNA construct. Preferred restriction sites are NcoI and BclI.

Thus, it is a further object of this invention to provide an immunoconjugate comprising of an amino acid (sequence) which is encoded by a DNA restriction site between antibody/antibody fragment and biologically active ligand, said restriction site being unique within the complete fusion construct. It is a further object of this invention to provide an immunoconjugate comprising a linker peptide between the antibody or antibody fragment and the biologically active ligand.

Furthermore, it is an object of the invention to provide an immunoconjugate, wherein the antibody or antibody fragment derives from murine, humanized or chimeric MAb 425, and is preferably selected from the group MAb 425-CH1/IL-8, MAb 425-CH2/(Ncol)/IL-8, MAb 425-CH2/(Bcll)/IL-8, MAb 425-Fv/IL-8, MAb 425-CH3/IL-8.

Furthermore, it is an object of the invention to provide a method for manufacturing an immunoconjugate as defined above and below and in the claims by fusing the DNA sequences encoding for the antibody or antibody fragment and the biologically active ligand with one another in an operable linkage on a single stranded DNA by means of an oligonucleotide which is complementary to the desired fusion DNA-sequence, placing the resulting construct into an expression vector which is transformed into the host organism, cultivating the host cells in a nutrient medium and expressing the fusion protein.

The immunoconjugates of this invention are suitable for therapeutic use. Thus, it is a further object of the invention to provide a pharmaceutical composition comprising at least of one of the immunoconjugates as defined above, below and in the claims and a physiologically acceptable carrier.

Upon further study of the specification and appended claims, further objects and advantages of this invention will become apparent to those skilled in the art.

BRIEF DESCRIPTION OF THE DRAWINGS

Various other objects, features and attendant advantages of the present invention will be more fully appreciated as the same becomes better understood when considered in conjunction with the accompanying drawings, wherein:

FIG. 1 shows models of antibody-cytokine immunoconjugates, wherein

C=cytokine
VH=heavy chain variable region
VL=light chain variable region
CH=constant region heavy chain
CL=constant region light chain;

column 8: MAb 425-CH2/(Ncol)/IL-8 supernatant 1:2 diluted*

* IL-8 concentration was determined by ELISA (Amersham)

vertical axis: number of cells per counted field;

* IL-8 concentration was determined by ELISA (Amersham);

vertical axis: optical density at 550 nm;

DETAILED DESCRIPTION OF THE INVENTION

This invention provides a fusion protein consisting of a monoclonal antibody or fragment thereof as a targeting element and a chemokine, e.g., IL-8, as an effector molecule with chemotactic and activating properties.

Figure 2:
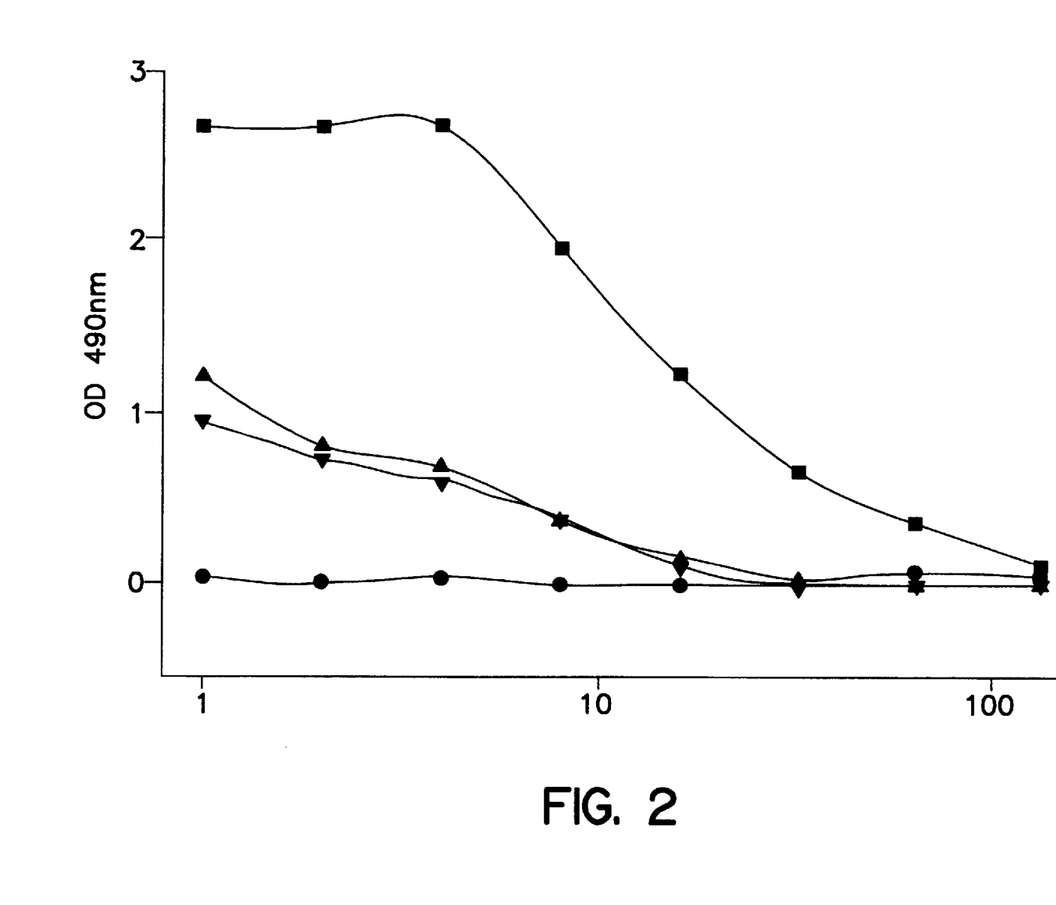
FIG. 2 is a demonstration of MAb 425 in COS-7 transfection-supernatants by anti-EGFR ELISA, wherein squares=MAb 425-CH3 supernatant
triangles=MAb 425-CH2/(Ncol)/IL-8 supernatant
reversed triangles=MAb 425-CH2/(Bcll)/IL-8 supernatant
dots=pHCMV supernatant
the horizontal axis=dilution of the supernatants; and
the vertical axis=optical density at 490 nm.

This invention provides, for the first time, a demonstration that IL-8 and other chemokines (such as MIPs) retain their biological activity when the N-terminus is blocked by additional amino acids such as the antibody moiety. Therefore, this molecule is useful in targeted tumor therapy in that effector cells are attracted to the EGF-receptor-positive tumor cells and activated in situ. It has also been shown that the cDNAs encoding the MAb 425 heavy chain and the IL-8 protein can be fused by molecular biology methods and proteins expressed in appropriate expression systems, and that the EGF-receptor-binding capacity is conserved in the fusion proteins (FIG. 2).

The main target cells of IL-8 are neutrophil granulocytes, which have three biological functions:

Chemotactic movement along a chemotactic gradient;

Release of stored granules with preproduced proteolytic enzymes;

Immediate production of superoxide anions (respiratory burst).

Figure 3A:
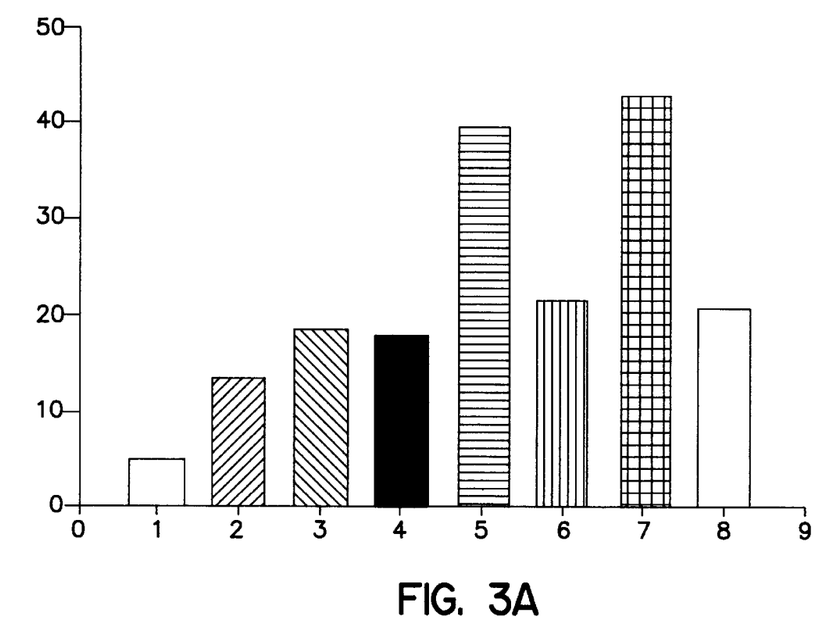
FIG. 3a shows the induction of chemotaxis by COS-7 transfection-supernatants, wherein column 1: control DMEM/PS
column 2: pHCMV supernatant undiluted
column 3: MAb 425-CH3 supernatant 1:14 diluted (according to the results of EGFR-ELISA)
column 4: MAb 425-CH3 supernatant 1:28 diluted (according to the results of EGFR-ELISA)
column 5: MAb 425-CH2/(Bcll)/IL-8 supernatant undiluted (1.76×10$^{-10}$ Mol/L*)
column 6: MAb 425-CH2/(Bcll)/IL-8 supernatant 1:2 diluted
column 7: MAb 425-CH2/(Ncol)/IL-8 supernatant undiluted (2.0×10$^{-10}$ Mol/L*)
Figure 3B:
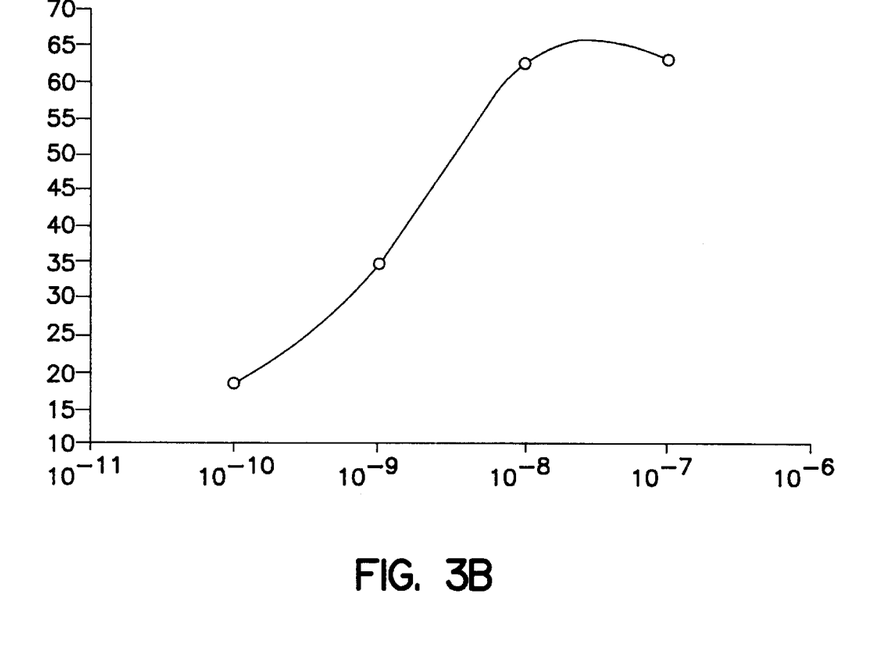
FIG. 3b shows the induction of chemotaxis by purified IL-8, wherein vertical axis: number of cells per counted field and
horizontal axis: concentration of IL-8 (Mol/L)
Figure 4:
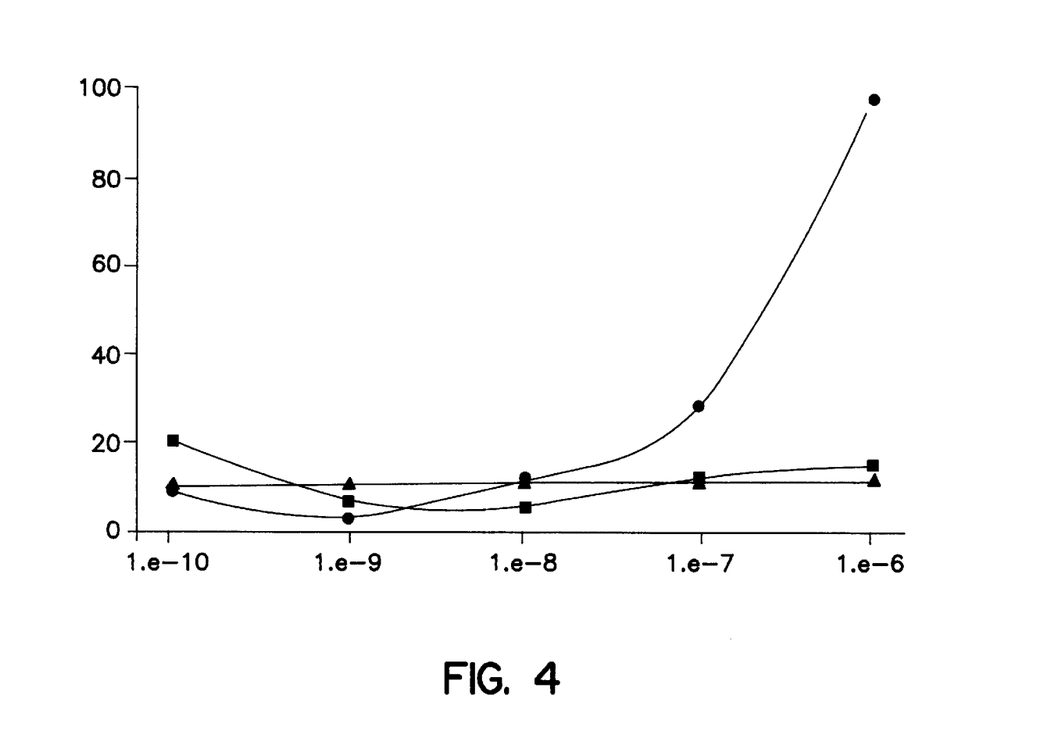
FIG. 4 shows the induction of chemotaxis by MAb 425-CH1/IL-8 (E. coli), wherein dots: MAb 425-CH1/IL-8 expressed in E. coli
squares: MAb 425-F(ab') expressed in E. coli
triangles: control Dulbecco's/BSA
vertical axis: number of cells per counted field, and
horizontal axis: concentration (Mol/L)

Accordingly, MAb 425/Ncol/IL-8 and MAb 425/Bcll/IL-8 fusion proteins were tested to determine whether the biological activity of the chemokine ligand portion of the fusion protein, e.g., the chemotactic activity, induction of MPO-release and superoxide release, was retained by the fusion product. Surprisingly, it was demonstrated that the fusion proteins according to the invention (for example MAb 425/Ncol/IL-8 and MAb 425/Bcll/IL-8) could in fact cause chemotactic activity, induction of MPO-release and superoxide release in their target cells. Results shown in FIG. 3a demonstrate that both fusion proteins are chemotactic for human neutrophils in the range of recombinant IL-8 (FIG. 3b). In addition to the MAb 425/Ncol/IL-8 and MAb 425/Bcll/IL-8 fusion proteins, which should assemble into a divalent form, a monovalent F(ab')/IL-8 fusion protein was created which was expressed in *E. coli* and purified. FIG. 4 shows that the F(ab')/IL-8 fusion protein is chemotactic for human neutrophils when compared to a MAb 425 F(ab'), expressed in *E. coli* and purified accordingly.

Figure 5:
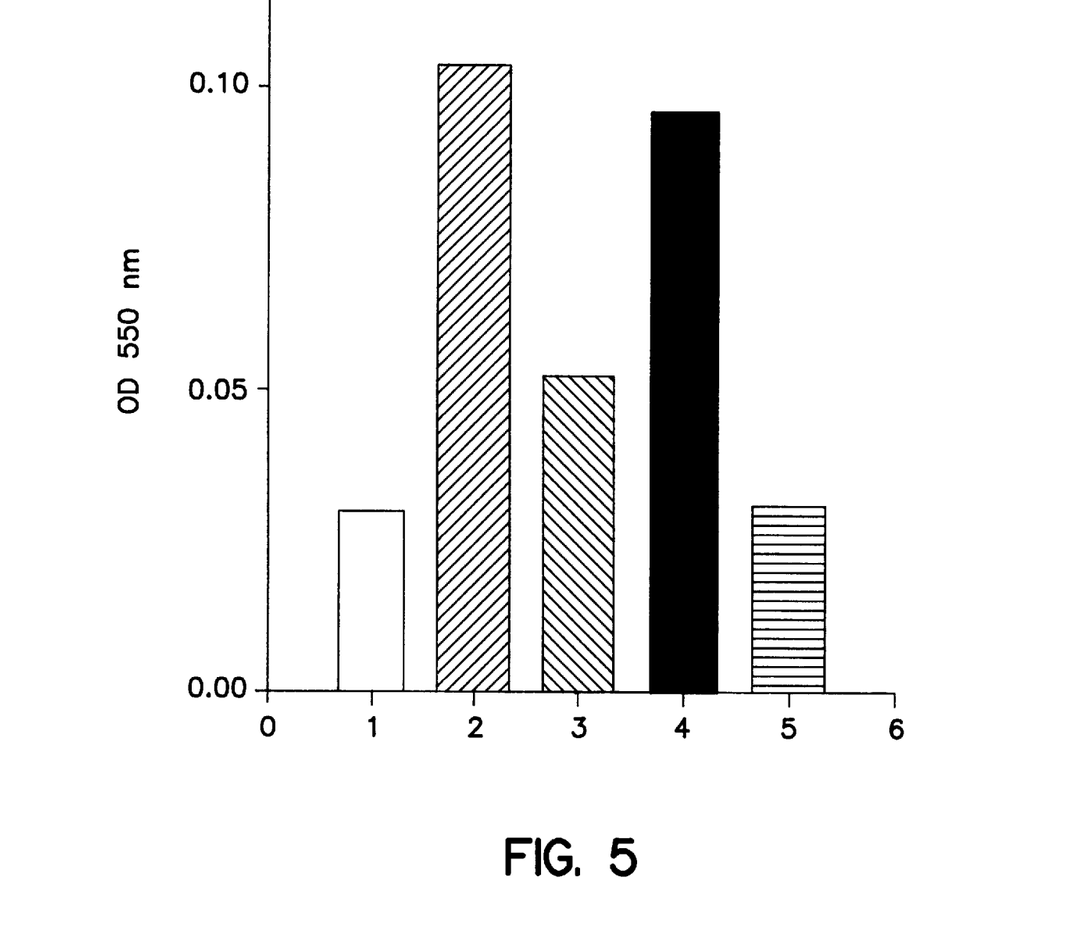
FIG. 5 shows the induction of superoxide release by COS-7-transfection-supernatants, wherein column 1: unstimulated cells
column 2: IL-8 10$^{-7}$M
column 3: MAb 425-CH2/(Ncol)/IL-8 supernatant undiluted (2.0×10$^{-10}$ Mol/L*)
column 4: MAb 425-CH2/(Bcll)/IL-8 supernatant undiluted (1.76 10$^{-10}$ Mol/L*)
column 5: MAb 425-CH3 supernatant undiluted (0 Mol/L*)

The MAb 425/Bcll/IL-8 fusion protein possesses rather strong capacity for superoxide release compared to free IL-8 (FIG. 5); the MAb 425/Ncol/IL-8 fusion protein is less active but values are significantly higher than control values (FIG. 5). MAb 425 alone shows no activity. All tests were performed using cytochalasine B as enhancer substance which alone shows no activity (data not shown).

Figure 6:
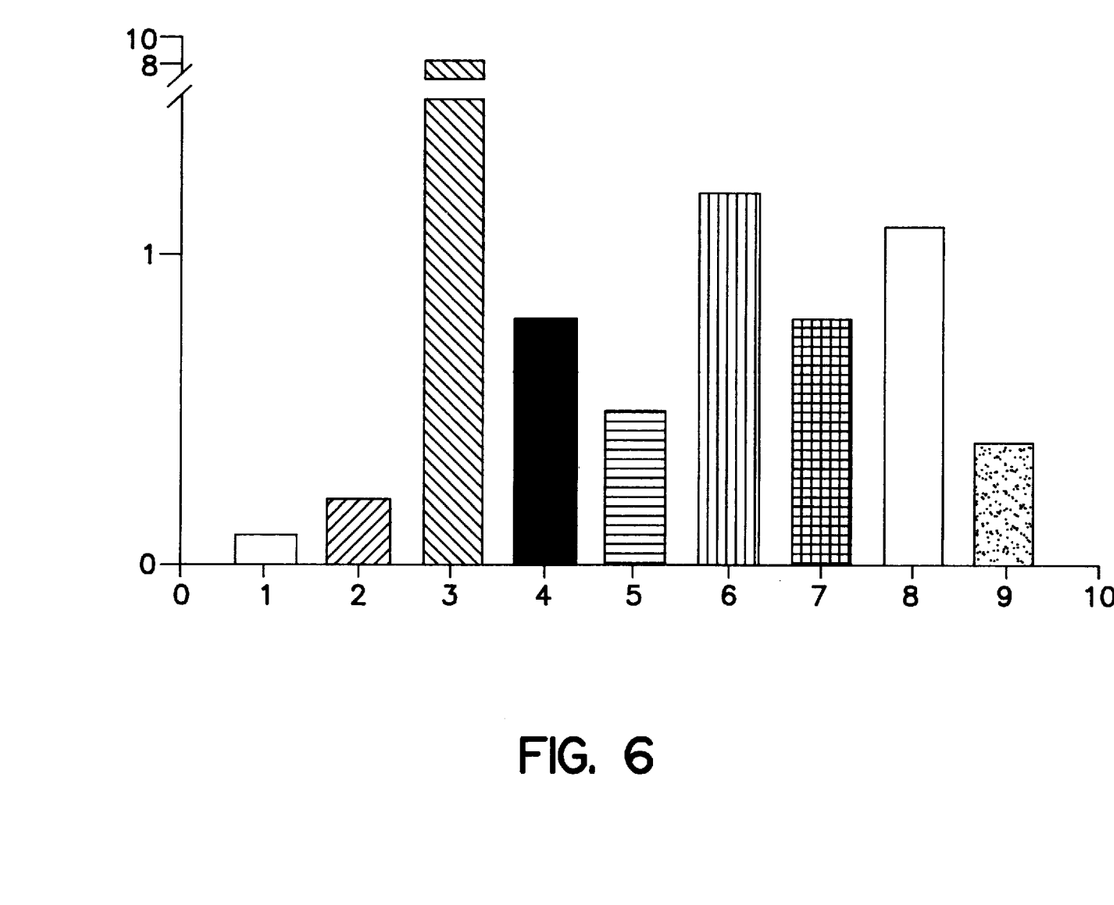
FIG. 6 shows the induction of MPO-release by COS-7-transfection-supernatants, wherein column 1: unstimulated cells
column 2: cytochalasine B stimulated cells
column 3: Il-8 10$^{-7}$M
column 4: MAb 425-CH3 supernatant undiluted
column 5: MAb 425-CH3 supernatant 1:2 diluted
column 6: MAb 425-CH2/(Ncol)/IL-8 supernatant undiluted
column 7: MAb 425-CH2/(Ncol)/IL-8 supernatant 1:2 diluted
column 8: MAb 425-CH2/(Bcll)/IL-8 supernatant undiluted
column 9: MAb 425-CH2/(Bcll)/IL-8 supernatant 1:2 diluted
vertical axis: % MPO activity compared to total MPO amount (100%).

Both fusion proteins induce myeloperoxidase (MPO)-release, but the MAb 425/Ncol/IL-8 fusion protein is more active than the MAb 425-/Bcll/IL-8 fusion protein (FIG. 6). All data are calculated accordingly to the data of the triton lysed cells, which is called 100% enzyme content. All data were generated using cytochalasine B as the enhancer substance.

It was demonstrated previously that the N-terminal portion of the IL-8 molecule with the highly conserved E-L-R-motif is required for receptor binding and signal transduction. The three dimensional structure of IL-8 is a homodimer in which both N-termini are in an exposed configuration. It was possible that the biological activity of IL-8 would be abrogated when the N-termini were blocked by additional amino acids. Therefore, restriction sites (Ncol/Bcll) were introduced between the two cDNAs to introduce linker peptides and thereby restore accessibility of the N-terminus.

Other approaches to create fusion proteins, such as chemical coupling of both elements, lead to rather undefined structures which might vary between batches. In addition, chemical coupling might destroy the secondary structure of the ligand or create a situation where most of the proteins are inactive with respect to receptor binding due to inaccessibility. In contrast, the approach according to the invention generates fusion proteins of defined structure which can be expressed in reproducible quality with almost no limitation.

The Mab 425-CH1/IL-8 (Fab/IL-8) fusion protein described herein provides a molecule according to the invention that combines the targeting property of an antibody specific for the tumor-associated EGF-receptor with the chemotactic and activating properties of IL-8. Since IL-8 is not species specific (Baggiolini et al., J. Clin. Invest. 84:1045–1049, 1989), the the anti-tumor potential of the fusion protein can be further assessed in a variety of suitable in vivo models, such as nude mice implanted with EGF-receptor-positive tumor cells, or in tumor-bearing scid mice reconstituted with human effector cells.

In summary, the fusion proteins according to the invention have the following properties:

binding to EGFR positive cells, causing chemotactic activity, inducing MPO and superoxide release, and/or inducing tumor lysis in situ.

Therefore, the immunoconjugates according to the invention are suitable for tumor therapy.

Still further, the immunoconjugates according to the invention can be used in in vitro as well as in vivo diagnosis of diseases or conditions in which EGFR is expressed. For example, the immunoconjugates can be labeled using routine methods of protein labeling with isotopic or enzymatically active reporter groups, bound to samples containing EGFR, and the concentration of EGFR thereby measured according to known methods. In addition, the immunoconjugates can labeled with physiologically acceptable reporter molecules which can be detected by various imaging modalities, injected into a patient and binding to tissues in which EGFR is expressed thereby detected.

Moreover, the immunoconjugates according to the invention can be used to purify EGFR from preparations containing them, or to purify cells which are expressing EGFR, by passing the EGFR in solution or on cells expressing it on the cell surface over an immobilized support media to which the immunoconjugates are bound, according to conventional methods.

Typically the immunoconjugates of this invention will be injected intravenously or parenterally. Generally, the dosage ranges for the administration of the immunoconjugates are large enough to produce the desired tumor-suppressing and tumor-lysing effect. The dosage, which can be routinely optimized, will depend on age, condition, sex and extent of the disease in the patient and can vary from 0.1 mg/kg to 200 mg/kg, preferably from 0.1 mg/kg to 100 mg/kg/dose in one or more doses administrations daily, for one or several days.

Preparations for parenteral administration include sterile aqueous or non-aqueous solutions, suspensions, and emulsions. Examples of non-aqueous solvents are propylene glycol, polyethylene glycol, vegetable oils such as olive oils, and injectable organic esters such as ethyl oleate and other solvents known in the art which are suitable for these purposes. The immunoconjugates of this invention can be used in a composition comprising a physiologically acceptable carrier. Examples of such suitable carriers are saline, PBS, Ringer's solution, or lactated Ringer's solution. Preservatives and other additives such as antibiotics, antioxidants, and chelating agents may also be present in the pharmaceutical formulations.

The pharmaceutical formulations of the present invention are suitable for the treatment of various types of tumors, including melanomas, gliomas and carcinomas, as well as blood tumors and solid tumors.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above and below, including EP 94114572.7, are hereby incorporated by reference.

EXAMPLES

Materials and Methods

Example A: General Remarks

All microorganisms, cell lines, plasmids, promoters, resistance markers, replication origins, restriction sites or other fragments of vectors which are mentioned in the application are commercially or otherwise generally available. Provided that no other hints are given, they are used only as examples and are not essential according to the invention and can be replaced by other suitable tools and biological materials, respectively.

The techniques which are essential according to the invention are described in detail below. Other techniques which are not described in detail correspond to known standard methods which are well known to a person skilled in the art or are described more in detail in the cited references and patent applications and in standard literature (e.g. "Antibodies, A Laboratory Manual", Harlow, Lane, Cold Sprng Harbor, 1988).

Example B: Monoclonal Antibodies

MAb 425 is an IgG1 murine monoclonal antibody raised against the human A 431 carcinoma cell line (ATCC CRL 1555). MAb 425 binds to a polypeptide epitope of the external domain of the human EGF-receptor and competes with the binding of EGF. MAb 425 was found to mediate tumor cytotoxicity in vitro and to suppress tumor cell growth of epidermoid and colorectal carcinoma derived cell lines in vitro (Rodeck et al., Cancer Res. 47:3692, 1987). Humanized and chimeric versions of MAb 425 have been disclosed in WO 92/15683.

Example C: Chemokines

Chemokine-encoding cDNAs were either purchased from British Biotechnology Limited (human IL-8 BBG 44: Herrmann Biermann GmbH, Bad Nauheim FRG) or generated from mRNA isolated from the cytokine producing human cell line U 937 (ATCC CRL 1593). Total RNA from chemokine-producing cells was isolated with RNAzol (WAK-Chemie, Germany) according to the manufacturer's instructions. The RNA was subsequently transcribed into cDNA and chemokine encoding sequences were PCR-amplified using appropriate primers deduced from published DNA-sequences.

Example D: Vectors pUC 19 is part of a series of related high copy number E. coli plasmid cloning vectors and contains portions of pBR322 and M13mp19. pUC 19 contains the inducible bacterial lac promotor-operator, followed by a multiple cloning site (Yanisch-Perron et al. Gene 33:103–109, 1985). pUC vectors are commercially available (e.g. New England Biolabs).

The pBluescipt KS/SK+ and KS/SK− phagemid vectors are derived from pUC19. The vectors are commercially available (Stratagene, Heidelberg).

The prokaryotic expression vectors are based on pSW1 vector (Ward et al., Nature 341:544–546, 1989), which is a derivative of the pUC19 vector. pSW1 contains a sequence coding for the leader peptide of the bacterial pelB gene from *Erwinia carotovora* (Lei et al., J. Bact 169:4379–4383, 1987). Foreign DNAs can be introduced in frame behind the pelB leader sequence to direct protein expression into the periplasm.

The eucaryotic expression vector pHCMV (Gillies et al., Cell 33:717, 1983) contains the origin of replication of the simian virus 40 (SV40) and the promotor and enhancer region of the human cytomegalovirus. The promotor/enhancer region is followed by a multi cloning site for the introduction of genes to be expressed. In this vector the chimeric form of the MAb 425 heavy chain variable region and the cy1CH2 region fused with the chemokine at the end of the CH2 domain were combined to generate a MAb 425 heavy chain fusion protein. The fusion Ig chain can be assembled into the immunoconjugate by combining it with the appropriate light chain to form a monovalent antigen-binding region, which can then be associated to produce a divalent immunoconjugate specific for the target antigen. The heavy and the light chain constructs can be placed in one or separate vectors.

Expression of Fusion Proteins in Eucaryotic Cells

Example 1: Construction of the Eucaryotic Expression Vectors for Fab 425-Chemokine Fusion Protein Expression A. Fusion of Mab 425 and Chemokines by PCR-Technology The human cy1 constant region was inserted into pUC 19 as a BamHl/BamHl fragment. The cy1 constant region contains two Sacll sites: one located in the 5' intron, 40 bp downstream of the 5' BamHl site and a second located 580 bp downstream of the 5' BamHl site and 140 bp upstream of the beginning of the CH3 domain. The second Sacll site is suitable for further subcloning and thus the first Sacll site was destroyed by introducing a SnaBl site with an adaptor. In this construct (ΔSacllcy1) fragments downstream from the Sacll site can easily be exchanged.

The human IL-8 was cut out of the pUC 18 vector (Bglll/EcoRl) and inserted into pBluescript SK+ (Stratagene GmbH, Heidelberg) (Smal/EcoRl), so that the Bglll and the Smal site were deleted. The Sacll/Xbal fragment of the ΔSacllcy1 clone was inserted into pBlue-skript SK+. Both genes were amplified with suitable primers (Table II), using PCR-technology:

for ΔSacllcy1:
    3' primer: end sequence of the CH2 domain and a Ncol-site
    5' primer: reverse sequencing primer for IL-8:
    3' primer: universal sequencing primer
    5' primer: a Ncol-site and the start sequence of IL-8

The products were cut and ligated with SK+ Sacll/EcoRl. In the resulting peptide sequence the C-terminal lysine of the CH2 domain is changed to methionine and the N-terminal serine of the Il-8 portion is changed to glycine.

The newly generated sequence at the junction between the two polypeptides is:

```
5' AAA GCC ATG GGT GCT 3'    (SEQ ID NO:1)
   Lys Ala Met Gly Ala       (SEQ ID NO:2)

cy1CH2    ←        →  IL-8 (2-72)
```

The same procedure was carried out using primers (Tab. 1) to introduce a Bcll site between the two genes. The resulting fusion gene has a Bcll-site between cy1 constant region gene and the IL-8 gene, encoding the full sequence of the CH2 domain, two additional amino acids (valine, isoleucine) and the IL-8 sequence without the first two amino acids (serine, alanine).

The newly generated sequence at the junction between the two polypeptides is:

5' GCC AAA GTG ATC AAA GAA 3'  (SEQ ID NO:3)
   Ala  Lys  Val  Ile  Lys  Glu    (SEQ ID NO:4)

cy1CH2 ⟵   ⟶ IL-8 (3-72)

PCR-products were subcloned into SK+ by using the SacII and EcoRl restriction sites. For eucaryotic expression these fusion genes were cloned into pHCMV-vector.

TABLE 1

Sequence of Primers Used for PCR to Generate Either a Ncol or a Bcll-Site, to create Fusion Proteins for Eucaryotic Expression

| Construct | Primer | DNA sequence | |
|---|---|---|---|
| CH2/Ncol | cy1 5' | 5'-CAGGAAACAGCTATGAC-3' | SEQ ID NO:5 |
| | cy1 3' | 5'-TGATCCATGGCTTTGGAGATGGTTTTCTCG-3' | SEQ ID NO:6 |
| IL-8/Ncol | IL-8 5' | 5'-GATCTACCTGCCATGGGTGCTAAAGAA-3' | SEQ ID NO:7 |
| | IL 8 3' | 5'-GTAAAACGACGGCCAGT-3' | SEQ ID NO:8 |
| CH2/Bcll | cy1 5' | 5'-CAGGAAACAGCTATGAC-3' | SEQ ID NO:9 |
| | cy1 3' | 5'-CGCGTGATCACTTTGGCTTTGGAGATGGTT-3' | SEQ ID NO:10 |
| IL-8/Bcll | IL-8 5' | 5'-CTCGTGATCAAAGAACTTAGATGTCAATGC-3' | SEQ ID NO:11 |
| | IL-8 3' | 5'-GTAAAACGACGGCCAGT-3' | SEQ ID NO:12 |

Example 2: Expression of the Immunoconjugates in Eucaryotic Cells

Expression of immunoconjugates in eucaryotic cells requires the introduction of vector DNA containing heavy and light chain into the host cells. A variety of different methods have been described such as electroporation, DEAE dextran, calcium phosphate, Lipofectin or protoplast fusion. Any host cell type may be used provided that the recombinant DNA sequences encoding the immunoconjugate are properly transcribed into mRNA in that cell type. Host cells may be mouse myeloma cells which do not produce immunoglobulin such as Sp2/0-AG14 (ATCC CRL 1581), P3X63Ag8.653 (ATCC CRL 1580) or hamster cells such as CHO-K1 (ATCC CCL 61), or CHO/DHFR- (ATCC CRL 9096), or BHK-21 (ATCC CCL 10). For transient expression, COS-1 (ATCC CRL 1650) or COS-7 (ATCC CRL 1651) may be used.

A: Transient Expression of Immunoconjugates

The expression vector pHCMV contains the origin of replication of the simian virus 40 (SV40). The cell line COS-7 is a derivative of the simian cell line CV-1 which has been transformed with an origin-defective SV40 virus. Therefore plasmids containing the SV40 origin of replication will be amplified and the production of immunoconjugates will be improved. Supernatants were harvested 72 hours later and tested for EGF-receptor binding and chemokine concentration by ELISA.

B. Permanent Expression of Immunoconjugates

Vectors containing recombinant constructs for the expression of immunoconjugates are introduced into appropriate host cells. The heavy and light chain constructs can be placed in the same or separate vectors; in the latter case both vectors may carry the identical selection marker such as Neomycin resistance or dehydrofolat reductase (DHFR), or two different selection markers to select for the presence of both vectors. Selection for the DHFR marker can only be performed in DHFR negative cell lines such as CHO/DHFR-. Mixed populations are analyzed for expression of immunoconjugates by EGF-receptor-specific ELISA. Further selection for positive monoclonals is done by limiting dilution cloning.

Example 3: Purification of Mab 425 Chemokine Immunoconjugates

MAb 425 immunoconjugates produced by the host cell may be collected and purified by any suitable method such as affinity chromatography using target antigen, anti-cytokine antibodies or anti-idiotypic antibodies (e.g. Harlow, Lane, I.c.).

In the present case the purification was achieved by anti-idiotypic antibodies which were produced from MAb 425 by standard methods (e.g., Kostelny et al. (1992), J. Immunol. 148:1547).

In order to obtain pure Fv-immunoconjugates, E. coli strains suitable for protein expression were transformed with the expression plasmids (see below). Cells were grown to $OD_{578}=0.5$ and induced with isopropyl-β-D-thiogalactopyranoside (IPTG) (1 mM). Cells were grown over-night and supernatants and cells were harvested. The supernatant was applied to an anti-MAb 425 anti-idiotypic column prepared according to standard procedures. The column was washed with phosphate buffered 0.5M NaCl, and bound proteins were eluted with 100 mM Glycine, 0.5M NaCl at pH 2.5. The eluate was immediately neutralized with Tris 2.5M pH 8.0. MAb 425-CH1/IL-8-containing fractions were pooled, concentrated and dialyzed against PBS.

Example 4: Construction of the Procaryotic Expression Vectors for Fab 425-Chemokine and $F_v$-Chemokine Fusion Protein Expression The Fv fragment was created according to Glockshuber et al. (Biochem. 29:1362–1367, 1990). The DNA sequences coding for the light chain and the Fd fragment of the heavy chain or the Fv fragment have been introduced into the multiple cloning site of the pSW1 vector. The mature light chain coding sequence, the heavy chain mature coding sequence and the Fv coding sequence are preceded by the leader peptide of the bacterial pelB gene. The heavy chain coding sequence contains a Ncol (3' end) site. The chemokine encoding cDNAs were modified by PCR to introduce the Ncol (5' end) and the Notl (3' end) or EcoRl (for Fv-fusion) restriction sites. The chemokine genes were fused in frame directly to the CH1 domain of the heavy chain or the Fv fragment. Alternatively, a linker peptide, such as (Gly-Gly-Gly-Gly-Ser)$_x$ (SEQ ID NO:13), wherein x is 1–4, can be introduced between the CH1 domain and the chemokine gene. Such linkers and methods to produce them are known in the literature (e.g., Curtis et al. 1991, Proc. Nat'l. Acad. Sci. U.S.A. 88:5809).

These vectors enable the efficient expression of functional F(ab') (=CH1) and Fv-chemokine fusion proteins in E. coli. The light chain and the heavy chain-chemokine fusion protein are located on a single dicistronic messenger RNA placed under the control of the inducible lac promotor (Skerra and Plückthun, Science 242: 1038–1040, 1988). Therefore, expression of the Fab/Fv-fusion protein can be induced according to the requirements for culture conditions. The translation of both proteins from a dicistronic messenger RNA favors synthesis of equal amounts of Fd-chemokine fusion protein and light chain thus increasing the chances for correct assembly into function Fab/Fv-fusion proteins. The two polypeptides are secreted into the periplasm of E. coli, where folding, formation of disulfide bonds and assembly into functional Fab 425-CH1/Fv fusion protein takes place. Prolonged culture of bacteria leads to a partial permeabilization of the outer membrane of E. coli permitting the diffusion of fusion proteins into the culture medium.

Example 5: Binding Properties of Mab 425 Immunoconjugates

The binding properties of the MAb 425 immunoconjugates were determined by EGF-receptor-specific ELISA. In brief, microtiter plates were coated over night at 4° C. with purified EGF-receptor. The plates were incubated with fusion protein-containing supernatants or supernatants containing unconjugated MAb fragments. Plates were washed to remove unbound material, and antibody bound to the EGF-receptor was detected by incubation with goat-anti-human IgG and IgM (heavy and light chain) conjugated to peroxidase, followed by substrate. The amount of bound EGF-receptor specific protein was determined by measuring at 490 nm.

Example 6: Biological Activity of Mab 425/IL-8 Immunoconjugates

A. Isolation of Effector Cells

For the determination of biological activity, human peripheral blood neutrophil granulocytes were freshly isolated from whole blood of healthy donors as previous described by Haslett et al. (Am. J. Pathol. 119:101–110, 1985). Plasma was separated by centrifugation, erythrocytes by dextran-sedimentation and at last the lymphocytes and leucocytes were separated by percoll-gradient centrifugation. The isolated neutrophils were used immediately.

B. Determination of Chemotactic Activity

Determination of chemotaxis was performed according to Falk et al. (J. Immunol. Methods 33:239–247, 1980). Briefly, a 48-well boyden chamber and 5 μm membranes was used. Purified neutrophils were resuspended in DMEM medium (DMEM, 1% Penicillin, 1% Streptomycin, 10% FCS, 2 mM L-Gluthamin, 1 mM Na-pyruvate, 10 mM HEPES) in a concentration of $1 \times 10^6$ cells/mL. The lower wells were loaded with the fusion-protein containing supernatants or control supernatants, covered with the membrane and finally the upper wells were loaded with the cell suspension. After incubation at 37° C. for 30 min the membranes were removed, and fixed in 2% glutardialdehyde for 10 min. Then, cells attached to the membrane were stained in Weigert's iron hematoxylin (Sigma diagnostic) for three minutes. The number of the cells bound to the membrane was determined microscopically.

C. Determination of the Capacity to Induce Enzyme Release in Neutrophils

To evaluate the capacity of the immunoconjugates on neutrophils to induce granula release, myeloperoxidase activity in the supernatant was monitored (Henson et al. J. Immunol. 121:851, 1978). The assay was performed in 96 well microtiter plates with $5 \times 10^5$ cells per well. After incubation (37° C.) with stimuli, plates were centrifuged and cell free supernatant was transferred to another 96 well microtiterplate. The cell-free supernatants were incubated with dianisidine (as substrate) and absorbance was measured at 492 nm. As a positive control, FMLP in $10^{-7}$M concentration was used. For determining total enzyme content cells without stimuli were lysed with Triton. Activity was calculated as percentage of the total enzyme content (lysis).

D. Determination of Superoxide Release Capacity

Cytochrome c is reduced by $O^{2-}$ and thereby changes its absorbance. The change in absorbance is a valuable marker for the estimation of superoxide activity. The assay was performed according to Guthrie et al. (J. Exp. Med. 160:1656–1671, 1984) in 96 well microtiterplates with $5 \times 10^5$ cells per well. After incubation with stimuli and cytochrome c, plates were centrifuged and the absorbance of the supernatant was determined at 550 nm.

Example 7: Further Immunoconjugates

According to the above description anti EGFR- CH1, -CH2-, CH3 and -Fv immunoconjugates (with/without restriction site and linker) were prepared and investigated, comprising of MIP-2α and MIP-2β as chemokine component. These constructs show similar properties as the IL-8 derivatives.

Example 8: Therapeutic Use of the Immunoconjugates

The immunoconjugates according to the invention can be administered to human patients for therapy. Therefore, it is an object of the invention to provide a pharmaceutical formulation comprising as the active ingredient at least one fusion protein defined above and in the claims, associated with one or more pharmaceutically acceptable carriers, excipients or diluents therefor.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An immunoconjugate comprising a fragment of a monoclonal anti-EGFR antibody, which specifically binds to an antigenic epitope of epidermal growth factor receptor (EGFR) on the surface of a tumor cell, fused to a chemotactically active ligand portion of the immunoconjugate, comprising IL-8, which has chemotactic activity for effector cells, wherein said antibody fragment and said ligand portion are directly fused or are fused by a linker peptide, with the proviso that the first N-terminal amino acid of IL-8 is or the first and second N-terminal amino acids of IL-8 are deleted and one or two additional amino acids are inserted therefor, whereby the native N-terminus of the IL-8 portion of the immunoconjugate is blocked and the imnmunoconjugate is chemotactically active.

2. An immunoconjugate of claim 1, wherein the antibody fragment is a Fab fragment or a F(ab')2 fragment comprises the complete variable region of the antibody (VL and VH domain) and the constant region domains CL and CHI, and optionally a hinge domain (antibody-CH1 conjugate).

3. An immunoconjugate of claim 1, wherein the antibody fragment comprises the complete variable region of the antibody (VL and VH domain) and the constant region domains CL, CH1 and CH2 (antibody-CH2 conjugate).

4. An immunoconjugate of claim 1, wherein the antibody fragment comprises the complete variable region of the antibody (VL and VH domain) and the constant region domains CL, CH1, CH2 and CH3 (antibody-CH3 conjugate).

5. An immunoconjugate of claim 1, wherein the antibody fragment comprises the complete variable region of the antibody (VL and VH domain) and a polypeptide sequence which links the VL and VH domains (antibody-Fv conjugate).

6. An immunoconjugate of claim 1, further comprising a linker peptide between the antibody fragment and the chemotactically active ligand portion.

7. An immunoconjugate of claim 6, wherein the linker peptide is encoded by a DNA restriction site,
   wherein said restriction site is operably linked to and between the DNA sequences encoding the antibody fragment and the chemotactically active ligand portion of a DNA construct encoding the immunoconjugate, and
   wherein said restriction site is unique within said DNA construct encoding the complete immunoconjugate.

8. An immunoconjugate of claim 1, wherein the antibody fragment is derived from murine, humanized or chimeric MAb 425.

9. An immunoconjugate of claim 1, selected from MAb 425-CH1/IL8, MAb 425-CH2/(Ncol)/IL-8, MAb 425-CH2/(Bcll)/IL-8, MAb 425-Fv/IL8, or MAb 425-CH3/Il-8.

10. A method for producing an immunoconjugate of claim 1, comprising
   fusing DNA molecules encoding, respectively, the antibody fragment and chemotactically active ligand portion of the immunoconjugate in an operable linkage with one another on a single stranded DNA, by means of a oligonucletide which is complementary to the desired fusion DNA sequence,
   placing the resulting construct into an expression vector which is transformed into a host organism,
   cultivating the transformed host in a nutrient solution, and
   expressing the fusion protein.

11. A method for producing an immunoconjugate of claim 1, comprising
   ligating DNA molecules encoding, respectively, the antibody fragment and chemotactically active ligand portion of the immunoconjugate in an operable linkage with one another and with an expression control sequence in an expression vector,
   transforming said expression vector construct into a host organism, and
   cultivating the transformed host in a nutrient medium under conditions whereby the immunoconjugate is expressed.

12. A pharmaceutical composition comprising an effective amount of an immunoconjugate of claim 1 and a physiologically acceptable carrier.

13. An immunoconjugate of claim 1, wherein the effector cells are neutrophil granulocytes or monocytes.

* * * * *